(12) United States Patent
Sawamura et al.

(10) Patent No.: US 9,403,740 B2
(45) Date of Patent: Aug. 2, 2016

(54) PROCESS FOR SEPARATION AND RECOVERY OF OLEFIN FROM MIXTURE OF PARAFFIN AND OLEFIN

(71) Applicant: Hitachi Zosen Corporation, Osaka-shi (JP)

(72) Inventors: Ken-ichi Sawamura, Osaka (JP); Kentaro Shinoya, Osaka (JP); Mai Tani, Osaka (JP); Suguru Fujita, Osaka (JP); Masashi Okada, Osaka (JP)

(73) Assignee: Hitachi Zosen Corporation, Osaka-shi (JP)

( * ) Notice: Subject to any disclaimer, the term of this patent is extended or adjusted under 35 U.S.C. 154(b) by 386 days.

(21) Appl. No.: 14/077,374

(22) Filed: Nov. 12, 2013

(65) Prior Publication Data
US 2014/0135559 A1    May 15, 2014

(30) Foreign Application Priority Data

Nov. 15, 2012  (JP) .................. 2012-250885

(51) Int. Cl.
*C07C 7/13* (2006.01)
*C07C 7/144* (2006.01)

(52) U.S. Cl.
CPC ........................ *C07C 7/13* (2013.01)

(58) Field of Classification Search
None
See application file for complete search history.

(56) References Cited

U.S. PATENT DOCUMENTS

| 5,670,051 | A | 9/1997 | Pinnau et al. |
| 5,769,927 | A | 6/1998 | Gottschlich et al. |
| 5,785,739 | A | 7/1998 | Baker |
| 6,361,582 | B1 | 3/2002 | Pinnau et al. |
| 6,414,202 | B1 | 7/2002 | Baker et al. |
| 6,428,606 | B1 | 8/2002 | Gottschlich et al. |
| 6,525,236 | B1 | 2/2003 | Baker et al. |
| 7,479,227 | B2 | 1/2009 | Da Costa et al. |
| 2014/0360939 | A1* | 12/2014 | Yamada ............... B01D 69/02 210/638 |

FOREIGN PATENT DOCUMENTS

| JP | 2006-508176 A | 3/2006 |
| WO | WO-2004/050590 A1 | 6/2004 |

OTHER PUBLICATIONS

Vladimiros Nikolakis et al., "Growth of a faujasite-type zeolite membrane and its application in the separation of saturated/unsaturated hydrocarbon mixtures," Journal of Membrane Science, vol. 184, 2001, pp. 209-219.

(Continued)

*Primary Examiner* — Tam M Nguyen
(74) *Attorney, Agent, or Firm* — Locke Lord LLP

(57) ABSTRACT

The invention provides a process for separation and recovery of an olefin from a mixture of a paraffin and an olefin, contains a separation membrane containing a porous substrate and a zeolite layer that is formed on a surface and/or in a surface layer of the substrate, the zeolite layer being a hydrophilic zeolite layer that has an Si/Al ratio of 1.3 Si/Al 3.5 and a separation factor α, which is expressed by a value of a water/IPA weight ratio of a permeated component divided by that of a feed component in a pervaporation test at a temperature of from 40 to 75° C. of a water-isopropanol mixture containing from 15 to 30% by weight of water, of 10 a 4,000.

8 Claims, 3 Drawing Sheets

(56) References Cited

OTHER PUBLICATIONS

Ioannis G. Giannakopoulos et al., "Separation of Propylene/Propane Mixtures Using Faujasite-Type Zeolite Membranes," Industrial & Engineering Chemistry Research, vol. 44, 2005, pp. 226-230.

Inés Tiscornia et al., "Separation of propylene/propane mixtures by titanosilicate ETS-10 membranes prepared in one-step seeded hydrothermal synthesis," Journal of Membrane Science, vol. 311, 2008, pp. 326-335.

* cited by examiner

US 9,403,740 B2

PROCESS FOR SEPARATION AND RECOVERY OF OLEFIN FROM MIXTURE OF PARAFFIN AND OLEFIN

BACKGROUND OF THE INVENTION

1. Field of the Invention

The present invention relates to an apparatus for separation and recovery of an olefin from a mixture of a paraffin and an olefin in the petroleum refining industries, petrochemical industries and the like, and a method therefor.

2. Background Art

An olefin, which is represented by ethylene and propylene, is a basic chemical material produced in the petroleum refining industries, petrochemical industries and the like, and in the production process and the utilization process thereof, an olefin is necessarily separated and recovered from a mixture of a paraffin and an olefin.

The separation of an olefin from an olefin-paraffin mixture is currently performed by distillation in general. However, due to the boiling points of an olefin and a paraffin, which are very close to each other, considerable energy is consumed in the separation by distillation, and a large-scale distillation tower having a large number of steps of from 120 to 180 is necessarily used.

Accordingly, considerable energy saving and simplification of the process may be realized by enabling highly selective permeation separation of an olefin from an olefin-paraffin mixture with a separation membrane.

U.S. Pat. Nos. 5,670,051, 5,769,927, 5,785,739, 6,361,582 B1, 6,414,202 B1, 6,428,606 B1, 6,525,236 B1 and 7,479,227 B1 propose enhancement of efficiency of the separation and recovery process of an olefin through membrane separation by Membrane Technology and Research, Inc.

These membrane processes are generally performed under high pressure, and therefore, the ordinary polymer membrane undergoes plasticization and loses the permeance and the separation selectivity. JP-T-2006-508176 proposes the use of a polyimide membrane that has good durability against plasticization, but the membrane has an extremely small permeance to an olefin.

Journal of Membrane Science, vol. 184, pp. 209-219 (2001) and Industrial & Engineering Chemistry Research, vol. 44, pp. 226-230 (2005) propose the use of crystalline porous aluminosilicate excellent in durability, such as zeolite, as a material for a separation membrane. However, it is the current situation that the separation membranes having been proposed have a very small permeance to an olefin. The smaller olefin permeance causes the necessity of a larger membrane area, which brings about increase of the cost of the equipments for membrane separation. Accordingly, the too small olefin permeance may lead difficulty in economy, and thus it is difficult to use the membranes in industry. For example, the zeolite membranes disclosed in the aforementioned two literatures have a propylene permeance of less than 100 GPU, but a ceramic film that can be industrially used necessarily has a propylene permeance of 300 GPU or more in consideration of economy. With respect to the unit of permeance, 1 GPU is equal to $10^{-8}$ cm$^3$ (STP: standard temperature and pressure)/(s·cm·cmHg) and $3.36 \times 10^{-10}$ mol/(m$^2$·s·Pa).

Journal of Membrane Science, vol. 311, pp. 326-335 (2008) reports the propylene-propane permeation separation factor of a separation membrane formed of crystalline porous titanosilicate. The membrane exhibits relatively good initial capability, i.e., a propylene permeance of 235 GPU and a separation factor (propylene/propane) of 5.5, but the literature reports that the permeation separation factor is largely deteriorated during the test for 15 days.

SUMMARY OF THE INVENTION

The invention has been made under the circumstances, and an object thereof is to provide an apparatus for separation and recovery of an olefin from a mixture of a paraffin and an olefin, the apparatus having a separation membrane that permeates an olefin with high selectivity and is excellent in durability, and to provide a method for separation and recovery of an olefin from a mixture of a paraffin and an olefin with high selectivity by using the apparatus.

The invention relates to, as a first embodiment, an apparatus for separation and recovery of an olefin from a mixture of a paraffin and an olefin, containing a separation membrane containing a porous substrate and a zeolite layer that is formed on a surface and/or in a surface layer of the substrate, the zeolite layer being a hydrophilic zeolite layer that has an Si/Al ratio of $1.3 \leq Si/Al \leq 3.5$ and a separation factor α, which is expressed by a value of a water/isopropanol weight ratio of a permeated component divided by that of a feed component in a pervaporation test at a temperature of from 40 to 75° C. of a water-isopropanol mixture containing from 15 to 30% by weight of water, of $10 \leq \alpha \leq 4{,}000$. Isopropanol may be hereinafter abbreviated as IPA in some cases.

The invention also relates to, as a second embodiment, a method for separation and recovery of an olefin from a mixture of a paraffin and an olefin, with an apparatus for separation and recovery of an olefin, containing a separation membrane containing a porous substrate and a zeolite layer that is formed on a surface and/or in a surface layer of the substrate, the zeolite layer being a hydrophilic zeolite layer that has an Si/Al ratio of $1.3 \leq Si/Al \leq 3.5$ and a separation factor α, which is expressed by a value of a water/IPA weight ratio of a permeated component divided by that of a feed component in a pervaporation test at a temperature of from 40 to 75° C. of a water-IPA mixture containing from 15 to 30% by weight of water, of $10 \leq \alpha \leq 4{,}000$.

In the first and second embodiments of the invention, the zeolite layer that is formed in a surface layer of the porous substrate means a zeolite layer having zeolite that is formed from the surface of the porous substrate to the surface layer thereof, into which the zeolite bites.

The invention also relates to, as a third embodiment, the method for separation and recovery of an olefin according to the second embodiment, wherein the olefin is propylene or ethylene.

The invention also relates to, as a fourth embodiment, the method for separation and recovery of an olefin according to the second or third embodiment, wherein the mixture of a paraffin and an olefin has a water content of −30° C. or less in terms of dew point.

The invention also relates to, as a fifth embodiment, the method for separation and recovery of an olefin according to any one of the second to fourth embodiments, wherein a membrane separation operation temperature is from 45 to 200° C.

In the method for separation and recovery of an olefin according to the invention, the zeolite layer is a hydrophilic zeolite layer that has an Si/Al ratio of $1.3 \leq Si/Al \leq 3.5$ and a separation factor α, which is expressed by a value of a water/IPA weight ratio of a permeated component divided by that of a feed component in a pervaporation test at a temperature of from 40 to 75° C. of a water-IPA mixture containing from 15 to 30% by weight of water, of $10 \leq \alpha \leq 4{,}000$. The separation membrane containing the zeolite layer and a porous substrate having the zeolite layer supported thereon is excellent in durability and permeates and recovers an olefin with high selectivity.

The mechanism of the selective permeation of an olefin may be derived from the fact that an olefin has higher affinity to zeolite than a paraffin. Zeolite having higher hydrophilicity generally has higher affinity to an olefin, but zeolite having too high hydrophilicity may strongly adsorb impurities, such as water, to cause permeation failure of an olefin. The affinity of an olefin and zeolite may also be influenced by the species of an exchangeable cation in the zeolite. The exchangeable cation species in zeolite in the invention is not particularly limited, and examples thereof include $Li^+$, $Na^+$, $K^+$, $Ag^+$, $Ca^{2+}$, $Sr^{2+}$, $Ba^{2+}$, $Cu^{2+}$, $Cu^+$ and $Zn^{2+}$.

In the method for separation and recovery of an olefin according to the third embodiment of the invention, the olefin is a low molecular weight compound having 2 or 3 carbon atoms, and therefore, the separation membrane may be free of clogging and may maintain the high permeance to the olefin.

In the method for separation and recovery of an olefin according to the fourth embodiment of the invention, the mixture of a paraffin and an olefin has a low water content of −30° C. or less in terms of dew point, and therefore, the high permeance to the olefin may be maintained.

In the method for separation and recovery of an olefin according to the fifth embodiment of the invention, the membrane separation operation is performed at a temperature of from 45 to 200° C., and thereby the high permeance to the olefin may be exhibited.

DESCRIPTION OF THE EMBODIMENTS

Figure 1:
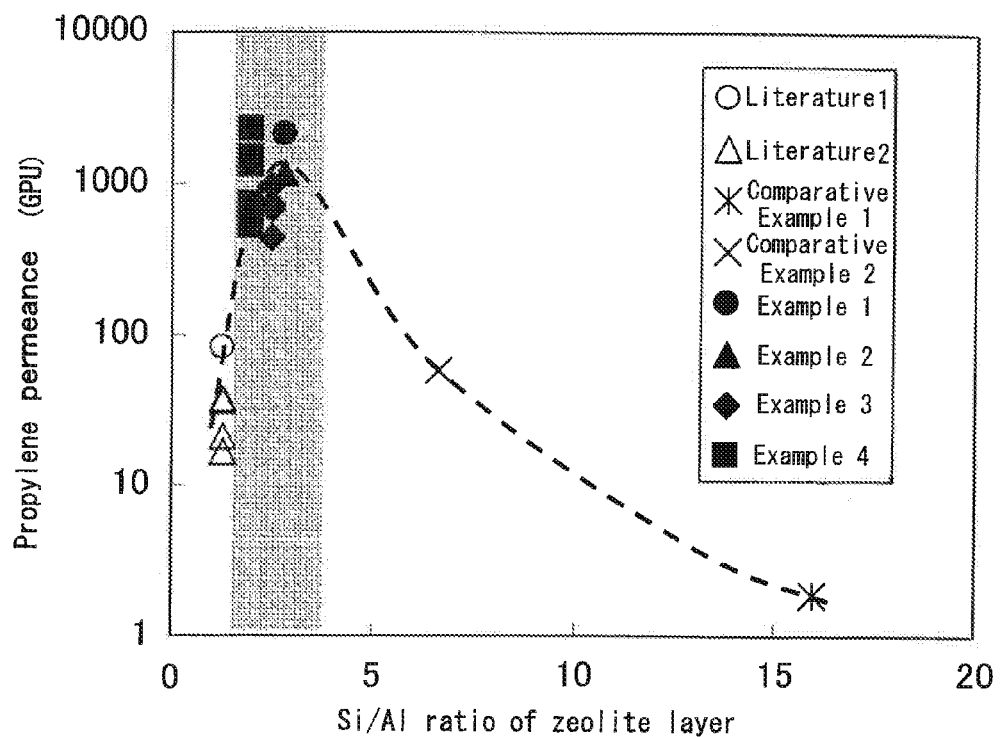
FIG. 1 is a graph showing the relationship between the Si/Al ratio and the propylene permeance of the hydrophilic zeolite layers.

Embodiment of the invention will be described below, but the invention is not limited thereto.

The invention relates to, in one embodiment, an apparatus for separation and recovery of an olefin from a mixture of a paraffin and an olefin, such as a mixture of ethane and ethylene, and a mixture of propane and propylene, and the apparatus is equipped with a separation membrane containing a porous substrate and a zeolite layer that is formed on a surface and/or in a surface layer of the substrate. The invention also relates to, in another embodiment, a method for separation and recovery of an olefin from a mixture of a paraffin and an olefin by using the apparatus.

In the apparatus for separation and recovery of an olefin according to the embodiment, examples of the material for the porous substrate include porous materials of alumina, silica, cordierite, zirconia, titania, vycor glass and a sintered metal, but the invention is not limited thereto, and various porous materials may be used. Examples of the shape of the porous substrate used include a tubular shape and a hollow fiber shape, but the invention is not limited thereto, and various shapes may be used. Preferred examples of the porous substrate include a ceramic porous tube formed by mixing, sintering and molding ceramic fine particles having a molar ratio of silica ($SiO_2$)/alumina ($Al_2O_3$) of from 2 to 750 and a metallic porous tube formed by molding a metal, such as stainless steel.

The zeolite layer is a hydrophilic zeolite layer that has an Si/Al ratio of $1.3 \leq Si/Al \leq 3.5$, and preferably $1.6 \leq Si/Al \leq 2.9$, and a separation factor α, which is expressed by a value of a water/IPA weight ratio of a permeated component divided by that of a feed component in a pervaporation test at a temperature of from 40 to 75° C. of a water-isopropanol mixture containing from 15 to 30% by weight of water, of $10 \leq \alpha \leq 4,000$, and preferably $100 \leq \alpha \leq 2,500$. When the Si/Al ratio is too small or too large, the olefin permeance may be lowered, and when α is too small or too large, the separation factor (olefin/paraffin) may be lowered, both cases of which are not preferred.

The mixture of a paraffin and an olefin preferably has a water content of −30° C. or less in terms of dew point, and more preferably −40° C. or less in terms of dew point.

The membrane separation operation temperature may be appropriately selected from a range of from 45 to 200° C., and preferably from 60 to 130° C., depending on the species of the paraffin and the olefin to be separated, and the like.

For forming the zeolite layer on the surface and/or in the surface layer of the porous substrate, such a method may be generally employed that zeolite crystal particles as seed crystals are attached in the form of a layer to the surface of the porous substrate (i.e., the primary growth), and are then grown through a hydrothermal synthesis reaction (i.e., the secondary growth).

Specific examples of the zeolite species used include FAU type, ZSM-5 type, MOR type and A type. The zeolite species preferably has an Si/Al ratio that is substantially the same as the zeolite that is to be secondarily grown through a hydrothermal synthesis reaction.

Examples of the method for coating the zeolite species on the surface of the substrate include a method of immersing the substrate in an aqueous slurry containing the zeolite species, followed by drying, and a method of coating the slurry on the substrate with a brush.

The secondary growth of the zeolite through a hydrothermal synthesis reaction will be described.

The raw materials used in the hydrothermal synthesis reaction include an alumina source and a silica source, and may also include an alkali metal source and/or an alkaline earth metal source depending on necessity. Examples of the alumina source include an aluminum salt, such as aluminum hydroxide, sodium aluminate, aluminum sulfate, aluminum nitrate and aluminum chloride, alumina powder and colloidal alumina. Examples of the silica source include an alkali metal silicate, such as sodium silicate, water glass and potassium silicate, silica powder, silicic acid, colloidal silica and a silicon alkoxide. Examples of the alkali metal source and the alkaline earth metal source include sodium oxide, sodium chloride, potassium chloride, calcium chloride and magnesium chloride. The molar ratio of the silica source and the alumina source ($SiO_2/Al_2O_3$) may be appropriately determined depending on the composition of the target zeolite.

The porous substrate having the seed crystals attached thereto may be immersed in an aqueous solution, an aqueous gel or an aqueous slurry containing the raw materials, and maintained under heated condition. The heating temperature is preferably from 40 to 200° C., and more preferably from 80 to 150° C. When the heating temperature is too low, the synthesis reaction of the zeolite may not be performed sufficiently, and when the heating temperature is too high, the synthesis reaction of the zeolite may be difficult to control, and a uniform zeolite layer may not be obtained. The heating time may be appropriately determined depending on the heating temperature, and is generally from 1 to 100 hours.

The zeolite layer formed on the surface and/or in the surface layer of the porous substrate, into which the zeolite bites, may be thus formed through a hydrothermal synthesis reaction. Zeolite layers having various compositions may be produced by the method.

EXAMPLE

Examples and Comparative Examples of the invention will be described in more detail with reference to figures below, but the invention is not limited thereto.

Example 1

Formation of Hydrophilic Zeolite Layer

An aqueous slurry containing FAU type zeolite powder as a zeolite species (Si/Al ratio of zeolite: 1.6 to 2.9) was coated on an outer surface of an α-alumina porous tube having an outer diameter of 1.6 cm and a length of 115 cm (produced by Hitachi Zosen Corporation) by an immersion method, and then dried to support zeolite crystal particles on the outer surface of the porous tube (i.e., the primary growth).

The porous tube having the zeolite supported thereon was then immersed in an aqueous gel containing an oxide mixture having a molar composition of $H_2O/Na_2O=57.4$, $Na_2O/SiO_2=1.3$, and $SiO_2/Al_2O_3=12.8$.

Hydrothermal synthesis was performed at a temperature of the gel of 100° C. for 4.75 hours for secondary growth of the zeolite crystal particles, thereby forming a zeolite layer having an Si/Al ratio of from 1.6 to 2.9 on the outer surface of the porous tube.

The separation membrane (membrane effective area: 500 cm$^2$) formed of the secondarily grown zeolite layer and the porous tube having the zeolite layer on the outer surface thereof was rinsed with pure water and then dried at room temperature over night and day.

Pervaporation Test

Figure 4:
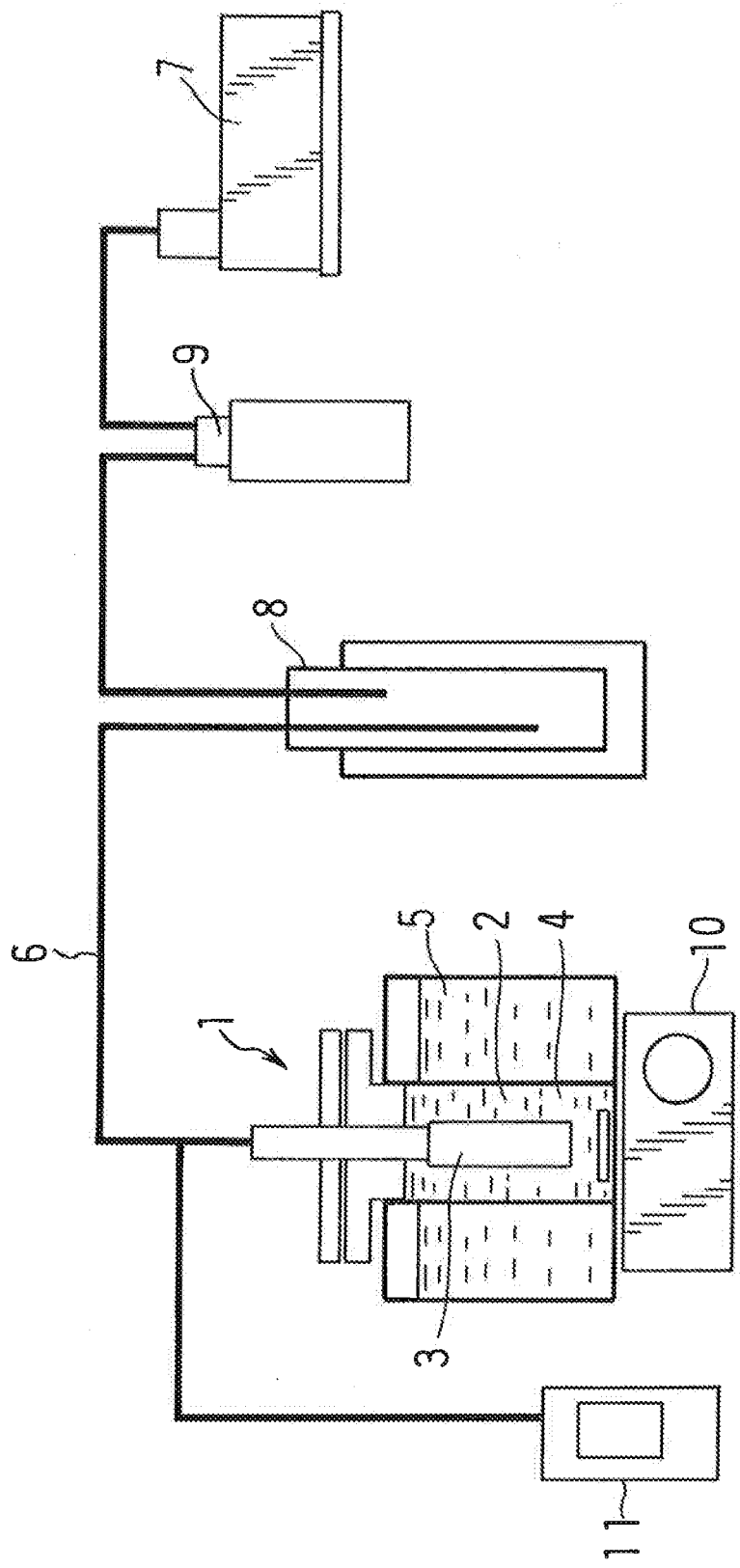
FIG. 4 is a schematic illustration showing a pervaporation test apparatus for water and IPA.

A separation of water was practiced with the separation membrane according to the invention by using a water/IPA pervaporation test apparatus shown in FIG. 4.

In FIG. 4, numeral 1 denotes a membrane separation apparatus, in which a separation membrane 3 is disposed in a solution tank 2 having a water/IPA mixed solution 4 containing from 15 to 20% by weight of water. The separation membrane 3 contains a porous tube and a zeolite layer formed on the outer surface thereof. The solution tank 2 is disposed in a thermostat chamber 5, by which the water/IPA mixed solution 4 is maintained at a temperature of 75° C.

The interior of the separation membrane 3 is vacuumed with a vacuum pump 7 through a vacuum line 6. A liquid nitrogen trap 8 and a vacuum trap 9 are disposed between the vacuum line 6 and the vacuum pump 7. The water/IPA mixed solution 4 in the solution tank 2 is uniformly stirred with a magnetic stirrer 10. A vacuum meter 11 is disposed in the course of the vacuum line 6 for measuring continuously the pressure on the permeation side (vacuum degree) of the separation membrane 3.

The component thus permeated through the membrane was collected through condensation and liquefaction in the liquid nitrogen trap 8, and measured for the IPA concentration with a refractive index meter (RX-5000 i-Plus, produced by Atago Co., Ltd.), from which the separation factor α, which is expressed by a value of a water/IPA weight ratio of a permeated component divided by that of a feed component was calculated. The results obtained are shown in Table 2.

Propylene-Propane Separation Test

For evaluating the olefin-paraffin permeation separation factor of the zeolite layer under high temperature and high pressure conditions, a specimen (effective membrane area: 10 cm$^2$) cut out from the zeolite layer (length: 115 cm, diameter: 1.6 cm) formed by the aforementioned method was disposed in the interior of a stainless steel module having heat resistance and pressure resistance.

In this test, propylene was used as the olefin, and propane was used as the paraffin, as representative examples. A mixed gas (water content: −30° C. or less in terms of dew point) of propylene (70% by mol) and propane (30% by mol) was fed to the membrane in the tubular shape from the outside thereof at 5 (STP) L/min and 8 atm, and the flow rate of the gas that was permeated to the interior of the membrane exposed to the atmosphere was measured with a gas flow meter. The concentration of the permeated component was measured by gas chromatography, and the separation factor (propylene/propane), which is expressed by a value of a propylene/propane molar ratio of a permeated component divided by that of a feed component was calculated. The results obtained are shown in Table 2.

Examples 2 to 4

A zeolite layer was formed on the outer surface of the porous tube in the same manner as in Example 1, and the resulting separation membrane was subjected to the pervaporation test and the propylene-propane separation test in the same manner as in Example 1. The results obtained are shown in Table 2.

It is understood that even when the zeolite layers are formed under the same conditions as in Example 1, there are fluctuations in separation factor α, which is expressed by a value of a water/IPA weight ratio of a permeated component divided by that of a feed component.

Comparative Examples 1 to 3

A zeolite layer was formed in the same manner as in Example 1 except that, in formation of a hydrophilic zeolite layer, powder of ZSM-5 type zeolite (Comparative Example 1), MOR type zeolite (Comparative Example 2) or A type zeolite (Comparative Example 3) was used as the zeolite species, and the materials for hydrothermal synthesis shown in Table 1 were used. The resulting separation membrane was subjected to the pervaporation test and the propylene-propane separation test in the same manner as in Example 1. The results obtained are shown in Table 2.

Test Results

Figure 2:
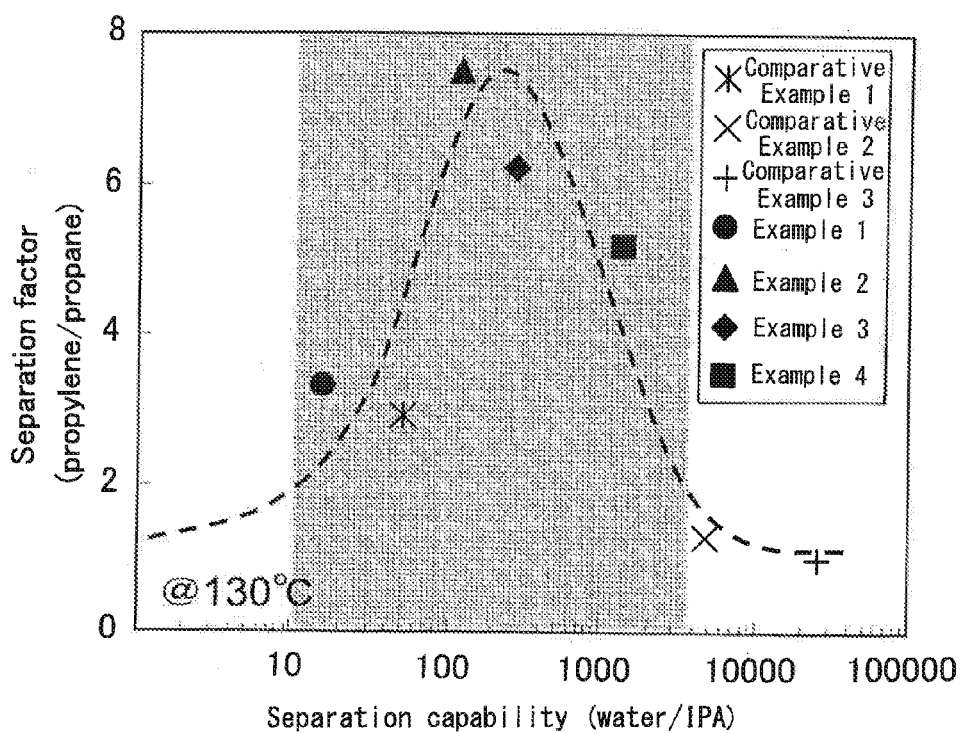
FIG. 2 is a graph showing the relationship between the separation factor α (water/IPA) and the separation factor (propylene/propane) of the hydrophilic zeolite layers.
Figure 3:
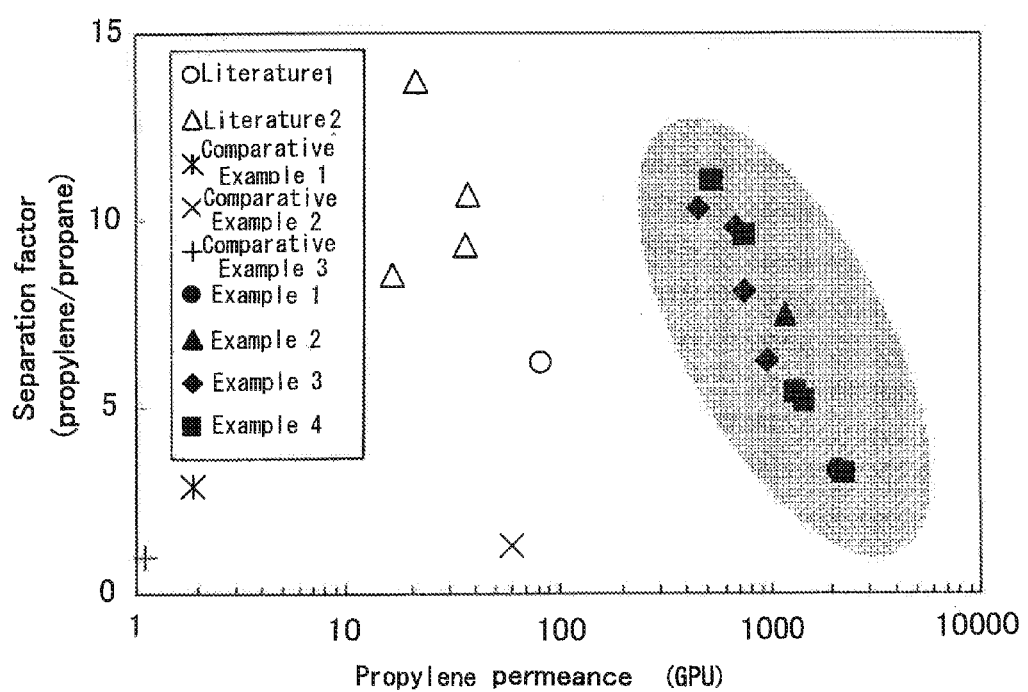
FIG. 3 is a graphs showing the relationship between the propylene permeance and the separation factor (propylene/propane) for comparing various zeolite membranes and the zeolite layers of the invention.

Graphs were prepared based on the test results shown in Table 2. FIG. 1 is a graph showing the relationship between the Si/Al ratio and the propylene permeance of the hydrophilic zeolite layers, FIG. 2 is a graph showing the relationship between the dehydration capability and the separation factor (propylene/propane) of the hydrophilic zeolite layers, and FIG. 3 is a graphs showing the comparison between the zeolite layers according to the invention and various zeolite layers. The terms "Literature 1" and "Literature 2" in FIGS. 1 and 3 show the faujasite type zeolite membranes disclosed in Journal of Membrane Science, vol. 184, pp. 209-219 (2001) and Industrial & Engineering Chemistry Research, vol. 44, pp. 226-230 (2005), respectively.

It is understood from FIGS. 1 to 3 as follows. The separation membranes of Examples exhibit a high olefin permeance (400 to 2,250 GPU) while maintaining the separation factor (olefin/paraffin)≥3 that is at least required for a zeolite membrane excellent in durability. As for the olefin permeance, the Si/Al ratio is preferably in a range of from 1.3 to 3.5, but is not preferably larger or smaller than the range. As for the olefin-paraffin separation factor, the separation factor α (water/IPA) is preferably in a range of from 10 to 4,000, but is not preferably larger or smaller than the range.

TABLE 1

Relationship between hydrothermal synthesis condition and Si/Al ratio

| | Synthesis | | Molar composition of gel for hydrothermal synthesis | | | |
|---|---|---|---|---|---|---|
| | temperature (° C.) | Synthesis time (Hr) | $H_2O/Na_2O$ | $Na_2O/SiO_2$ | $SiO_2/Al_2O_3$ | Si/Al ratio |
| Examples 1 to 4 | 100 | 4.75 | 57.4 | 1.3 | 12.8 | 1.6 to 2.9 |
| Comparative Example 1 | 180 | 18 | 120 | 0.28 | 240 | 12 to 18 |
| Comparative Example 2 | 170 | 12 | 115 | 0.28 | 240 | 5.6 to 10.3 |
| Comparative Example 3 | 105 | 4.25 | 75 | 1 | 2 | 1 |

TABLE 2

Test results of pervaporation test of hydrophilic zeolite layers

| | Si/Al ratio of zeolite layer | Separation factor α (water/IPA) | Propylene permeance (GPU) | Separation factor (propylene/propane) | Test temperature (° C.) |
|---|---|---|---|---|---|
| Literature 1 | 1 to 1.5 | — | 83 | 6.2 | 40 |
| Literature 2 | 1 to 1.5 | — | 21 | 13.7 | 100 |
| | | | 37 | 10.7 | 90 |
| | | | 36 | 9.3 | 90 |
| | | | 16 | 8.5 | 100 |
| Example 1 | 1.6 to 2.9 | 16 | 2,128 | 3.3 | 130 |
| Example 2 | 1.6 to 2.9 | 118 | 1,158 | 7.5 | 130 |
| Example 3 | 1.6 to 2.9 | 277 | 449 | 10.3 | 60 |
| | | | 674 | 9.8 | 80 |
| | | | 740 | 8.1 | 110 |
| | | | 959 | 6.2 | 130 |
| Example 4 | 1.6 to 2.9 | 1,367 | 516 | 11.0 | 60 |
| | | | 743 | 9.5 | 80 |
| | | | 1,335 | 5.4 | 110 |
| | | | 1,464 | 5.1 | 130 |
| | | | 2,236 | 3.2 | 150 |
| Comparative Example 1 | 12 to 16 | 51 | 1.9 | 2.9 | 130 |
| Comparative Example 2 | 5.6 to 10.3 | 4,763 | 59 | 1.3 | 130 |
| Comparative Example 3 | 1 | 25,540 | 1.1 | 1 | 130 |

What is claimed is:

1. A method for separation and recovery of an olefin from a mixture of a paraffin and an olefin, with an apparatus for separation and recovery of an olefin, containing a separation membrane containing a porous substrate and a zeolite layer that is formed on a surface and/or in a surface layer of the substrate, the zeolite layer being a hydrophilic zeolite layer that has an Si/Al ratio of 1.3≤Si/Al≤3.5 and a separation factor α, which is expressed by a value of a water/isopropanol weight ratio of a permeated component divided by that of a feed component in a pervaporation test at a temperature of from 40 to 75° C. of a water-IPA mixture containing from 15 to 30% by weight of water, of 10≤α≤4,000.

2. The method for separation and recovery of an olefin according to claim 1, wherein the olefin is propylene or ethylene.

3. The method for separation and recovery of an olefin according to claim 1, wherein the mixture of a paraffin and an olefin has a water content of −30° C. or less in terms of dew point.

4. The method for separation and recovery of an olefin according to claim 1, wherein a membrane separation operation temperature is from 45 to 200° C.

5. The method for separation and recovery of an olefin according to claim 2, wherein the mixture of a paraffin and an olefin has a water content of −30° C. or less in terms of dew point.

6. The method for separation and recovery of an olefin according to claim 2, wherein a membrane separation operation temperature is from 45 to 200° C.

7. The method for separation and recovery of an olefin according to claim 3, wherein a membrane separation operation temperature is from 45 to 200° C.

8. The method for separation and recovery of an olefin according to claim 5, wherein a membrane separation operation temperature is from 45 to 200° C.

* * * * *